US011219193B2

(12) United States Patent
Maurice

(10) Patent No.: US 11,219,193 B2
(45) Date of Patent: Jan. 11, 2022

(54) INSTRUMENTED DEVICE FOR CHARACTERISING THE CAPACITY OF A MOUSE TO ORIENTATE ITSELF

(71) Applicants: UNIVERSITE DE MONTPELLIER, Montpellier (FR); INSERM-INSTITUT NATIONAL DE LA SANTE ET DE LA RECHERCHE MEDICALE, Paris (FR); ECOLE PRATIQUE DES HAUTES ETUDES, Paris (FR)

(72) Inventor: Tangui Maurice, Saint-Gely-du-Fesc (FR)

(73) Assignees: UNIVERSITÉ DE MONTPELLIER, Montpellier (FR); INSTITUT NATIONAL DE LA SANTE ET DE LA RECHERCHE MEDICALE—INSERM, Paris (FR); ÉCOLE PRATIQUE DES HAUTES ÉTUDES, Paris (FR)

( * ) Notice: Subject to any disclaimer, the term of this patent is extended or adjusted under 35 U.S.C. 154(b) by 748 days.

(21) Appl. No.: 15/746,343

(22) PCT Filed: Jul. 22, 2016

(86) PCT No.: PCT/EP2016/067520
§ 371 (c)(1),
(2) Date: Jan. 19, 2018

(87) PCT Pub. No.: WO2017/017010
PCT Pub. Date: Feb. 2, 2017

(65) Prior Publication Data
US 2018/0206447 A1    Jul. 26, 2018

(30) Foreign Application Priority Data

Jul. 24, 2015 (FR) ...................................... 1557093

(51) Int. Cl.
*A01K 1/03* (2006.01)
*A61B 5/16* (2006.01)
(Continued)

(52) U.S. Cl.
CPC ............ *A01K 1/031* (2013.01); *A01K 5/0233* (2013.01); *A01K 7/06* (2013.01); *A01K 15/02* (2013.01);
(Continued)

(58) Field of Classification Search
CPC ........ A01K 1/03; A01K 1/031; A01K 5/0233; A01K 7/06; A01K 15/02; A01K 15/027;
(Continued)

(56) References Cited

U.S. PATENT DOCUMENTS 4,337,726 A * 7/1982 Czekajewski ........ A01K 29/005
119/421
4,448,150 A * 5/1984 Catsimpoolas ...... A01K 29/005
119/455
(Continued)

FOREIGN PATENT DOCUMENTS

CN    101884306 A    11/2010
CN    201995441 U    10/2011

OTHER PUBLICATIONS

International Search Report from International Patent Application No. PCT/EP2016/067520, dated Oct. 24, 2016.

*Primary Examiner* — Ebony E Evans
(74) *Attorney, Agent, or Firm* — Greer, Burns & Crain, Ltd.

(57) ABSTRACT

A device is provided for studying the ability of at least one mouse to find its bearings in a maze, the device including a plurality of houses distributed around a central agora and in which at least one stimulator allows the at least one mouse to carry out certain activities and/or satisfy certain primary
(Continued)

needs. Each house further includes at least one sensor for measuring the activity of the mouse in the house, and more particularly its use of the at least one stimulator. Finally, a sensor makes it possible to detect and measure the movements of each mouse in the device. Quantitative parameters originating from these measurements thus make it possible to highlight the quality of the geographical memory of the at least one mouse.

14 Claims, 2 Drawing Sheets

(51) Int. Cl.
| | | |
|---|---|---|
| *A01K 15/02* | (2006.01) | |
| *A61B 5/11* | (2006.01) | |
| *A61B 5/00* | (2006.01) | |
| *A01K 5/02* | (2006.01) | |
| *A01K 7/06* | (2006.01) | |
| *A01K 29/00* | (2006.01) | |

(52) U.S. Cl.
CPC .......... *A01K 15/027* (2013.01); *A01K 29/005* (2013.01); *A61B 5/1105* (2013.01); *A61B 5/1113* (2013.01); *A61B 5/165* (2013.01); *A61B 5/4088* (2013.01); *A61B 5/1122* (2013.01); *A61B 2503/40* (2013.01); *A61B 2503/42* (2013.01)

(58) Field of Classification Search
CPC ..... A01K 29/005; A61B 5/165; A61B 5/1113; A61B 5/4088; A61B 5/1105; A61B 2503/40; A61B 2503/42
USPC ........................................................ 119/421
See application file for complete search history.

(56) References Cited

U.S. PATENT DOCUMENTS

| | | | | |
|---|---|---|---|---|
| 4,574,734 | A * | 3/1986 | Mandalaywala | A01K 1/031 119/421 |
| 5,372,093 | A * | 12/1994 | Pooshs | A01K 5/0291 119/51.11 |
| 6,234,111 | B1 * | 5/2001 | Ulman | A01K 1/031 119/51.02 |
| 6,899,686 | B2 * | 5/2005 | Hampton | A61B 5/1038 600/595 |
| 7,121,229 | B2 * | 10/2006 | Hong | A01K 1/031 119/421 |
| 8,634,635 | B2 * | 1/2014 | Bai | A01K 29/005 382/154 |
| 9,485,966 | B1 * | 11/2016 | Betts-Lacroix | G05D 23/27 |
| 10,650,228 | B2 * | 5/2020 | Roberson | G06K 9/00362 |
| 2003/0024482 | A1 * | 2/2003 | Gondhalekar | A01K 1/031 119/417 |
| 2012/0180731 | A1 * | 7/2012 | Garner | A01K 1/031 119/417 |
| 2013/0233249 | A1 * | 9/2013 | Zhu | A01K 1/031 119/452 |
| 2014/0167958 | A1 * | 6/2014 | Kimchi | A01K 29/005 340/539.13 |
| 2017/0064929 | A1 * | 3/2017 | Yakovenko | A61B 5/1038 |
| 2017/0308755 | A1 * | 10/2017 | Ala-laurila | G06K 9/00744 |
| 2019/0117145 | A1 * | 4/2019 | Koronyo | A01K 15/02 |

* cited by examiner

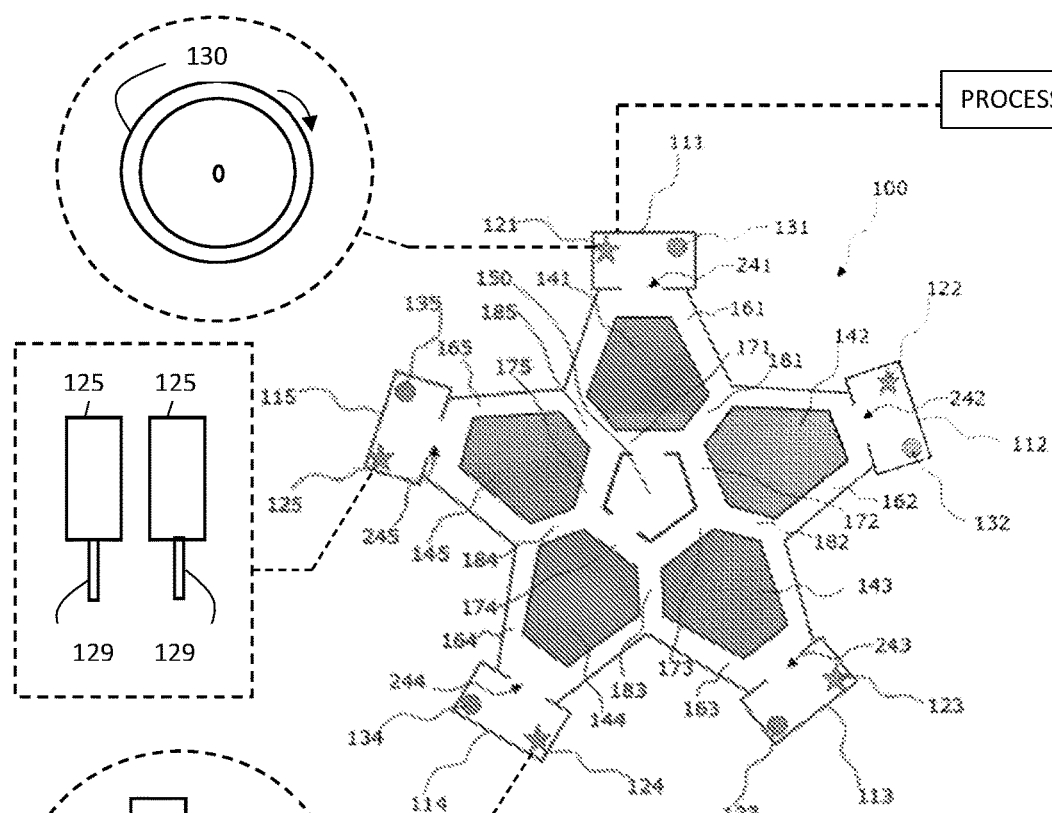
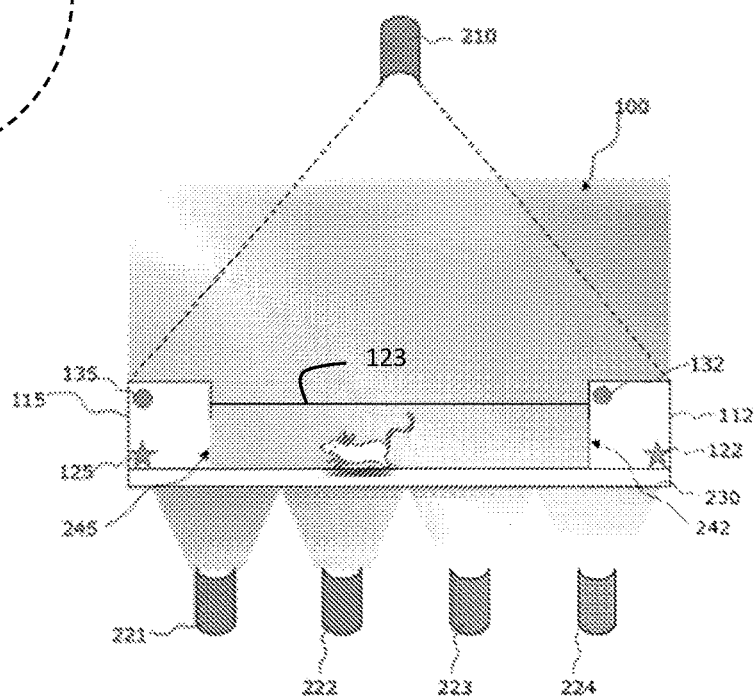
Figure 1
Figure 2

INSTRUMENTED DEVICE FOR CHARACTERISING THE CAPACITY OF A MOUSE TO ORIENTATE ITSELF

BACKGROUND

The present invention relates to a device for studying the ability of at least one mouse to orientate itself in a maze involving topographical memory and spatial memory.

The present invention relates to the field of laboratory instrumentation, and more particularly that intended for analyses of behaviour and learning in laboratory animals.

In a known manner, an early sign of the development of pathological ageing or of dementia, for example of the Alzheimer's type, is disorientation in a familiar environment. However, there is at present no behavioural procedure in animal studies that tackles characterization of the ability of such an individual to find its bearings in a familiar environment, i.e. with which the animal has previously been familiar for a considerable time.

A device is known comprising a central platform and various boxes containing food, connected to the central platform by a channel equipped with an opaque door (CN 101 884 306A).

A memory training device for animals is also known, constituted by a maze and comprising a central rotating device, connected to a motor (US 2013/0233249).

A device of the maze type for rats is also known, comprising several rows of stacked training boxes, with communication between adjacent cages, in particular by a ladder (CN 201995441 U).

There is a known document by G. Winocur et al. Neurobiology of Aging, 31 (2010), 143-150, "A study of remote spatial memory in aged rats", in which a population of rats is introduced into a complex environment comprising a plurality of compartments making it possible to satisfy one of the rats' particular needs (playing, eating, drinking, interacting). This document does not make it possible to test the rats' orientation faculties inside the complex environment as all the compartments are visible to the rats all the time. Moreover, the various activities offered to the rats in the compartments are not recorded and no quantitative data relating to the use of said activities are measured. Finally, this test has only been described for rats and is not suitable for mice. Up to now it has been used in pharmacological studies after hippocampal lesion, but not in the context of Alzheimer's disease.

In fact, the behavioural tests used at present (tests of activity, memory, anxiety, response to stress, addiction, etc.) are strongly dependent on the animal species used, or even on the strain used of the species under consideration. Thus, very often, tests intended for rats and for mice are different, as the mouse is for example more mobile and exploratory than the rat, whereas the latter is more competent in the procedures. Measurement of complex behavioural responses therefore requires the development of new behavioural tests that are particularly suited to the species under consideration.

Various animal behaviour tests are used at present in behavioural neuropharmacology. However, none specifically addresses topographical memory in mice. The reference tests address spatial memory, such as learning in a circular swimming pool popularized by Richard Morris, or learning in a radial arm maze with eight arms that allows simultaneous analysis of errors of reference memory and of working memory. These tests have the advantage that they are used for rats and mice. However, they are essentially relevant for measuring defects in learning.

The aim of the present invention is to respond at least in large part to the above problems and moreover to provide other advantages.

Another aim of the invention is to provide directly a test usable for all the lines of transgenic mice that model Alzheimer's disease. Another aim of the invention is more effective and accurate measurement of the orientation faculties of a mouse population.

Another aim of the invention is to provide a test making it possible to characterize autism, and/or feeding behaviour, and/or social interaction and/or the sciences of movement and/or the state of depression of a mouse population.

Another aim of the invention is to offer a novel automated platform for analysing the behaviour of mice in a complex environment.

SUMMARY

At least one of the aforementioned aims is achieved with a device for studying the topographical memory of at least one mouse, said device comprising:
- a central space, called the agora, at least partially closed and open on at least one side,
- a plurality of closed spaces, called houses, located at the periphery of the agora, said houses being open on one side and connected to at least one traffic space, called street, allowing the at least one mouse to reach the agora,
- a plurality of means for stimulating the at least one mouse located in the plurality of houses, said at least one traffic space forming a maze that is arranged in such a way that the distances between the agora and each house are identical, each house being accessible from the agora via at least two direct paths of the same length, all of the direct paths connecting each house to the agora being of equal length. Optionally, these traffic spaces can be closed at certain defined positions by doors, in order to analyse the exploration strategy adopted by the mice.

It is thus possible to put a mouse population inside a special structure that will stimulate their orientation faculties, their topographical memories of said structure and more particularly of the houses in which the mice will find activities and rewards. Preferably, 6 to 8 individuals are placed in said structure.

The agora is an uncovered central space, open on at least one side to the traffic spaces of the device. The mice are placed in the agora at the start of an experiment.

The houses are located all around the agora, and at an equal distance from the latter, so that the length of the possible paths for reaching it is identical for all the houses when starting from the centre of the device. Thus, the probability that a healthy mouse, not already familiar with the device, will reach any one of the houses is identical.

A direct path is constituted by the smallest combination of streets taken for going from one point to another. A direct path is that taken by the at least one mouse for reaching a given destination, one of the houses, as quickly as possible, without making a U-turn and/or without taking a street that does not lead to the desired place.

The traffic spaces can be closed temporarily or permanently at certain positions by means of doors, in order to analyse the exploration strategy adopted by the at least one mouse.

Preferably, all the houses are located on a single level, and/or are distributed around the agora according to a star plan, each house being located at one point of said star. Advantageously, the agora is organized according to a five-pointed star plan.

More particularly, the device according to the first aspect of the invention further comprises:
  a plurality of sensors, preferably located in the houses, and arranged for measuring the activity of the at least one mouse with said means of stimulation, and
  a processing unit programmed for determining behavioural parameters of the at least one mouse in said device from measurements made by the plurality of sensors.

The processing unit is programmed for processing the information returned by the various sensors and/or instruments and/or cameras of the device. Preferably, said returned information is processed in real time. The processing unit is programmed for recording the information collected according to a special protocol making it possible to select information of interest from all of the instrumental data. By way of non-limitative examples, the protocol allows the user to display areas of interest on the device, mouse monitoring thresholds, acquisition times, acquisition frequencies of the sensors and/or the sampling frequencies of the cameras.

Advantageously, the device can further comprise a control unit arranged for modifying the operating parameters of the sensors and/or cameras and/or light sources and/or instruments of said device. The control unit is connected to at least some of the cameras and/or light sources and/or sensors and/or instruments of said device by wire or wirelessly, and is configured for transmitting configuration parameters and/or receiving data.

The activity of the mice in the device is measured, both in the various houses and in the traffic spaces, by means of the plurality of sensors located in the device, thus making it possible to collect quantified or quantifiable data relating to the behaviour of the mice in the device. By way of non-limitative examples, the following parameters finally make it possible to characterize, in a quantifiable manner, certain aspects of the behaviour of the mice and of their faculty for orientation in the device:
  the number of times each mouse enters each house,
  the travel time for going to the various houses,
  the number of errors for reaching the various houses, an error being regarded as entering a street that does not correspond to the shortest path to get there,
  the total path travelled in the traffic spaces,
  the number of times each of the traffic spaces is entered,
  the location of each mouse in the device,
  the locomotion of the mice,
  the speeds of movement of each mouse,
  the interactions between the different mice present in the device,
  the number and position of the U-turns made by each mouse in the traffic spaces,
  the number and position of the rearing activities of each mouse in the device,
  the number and position of the grooming activities of each mouse in the device,
  the time spent in each house.

They can be parameters directly measured by sensors, video monitoring or extracts of the data measured and then calculated.

For this purpose, the mice are introduced into it preferably according to a particular protocol comprising two phases:
  a first phase of learning, during which the mice freely explore the device and the various houses, and preferably in a group of several individuals (for example 6-8). This first phase thus allows the mice introduced into the device to memorize the location of the various houses, the various paths that lead them there, and to become familiar with the type of activity that they will find there;
  a second phase of simulation of the mice's topographical memory, during which they are put in a state such that they try preferentially to reach a particular house.

The first phase of learning comprises several sessions of variable duration. For example, the learning phase can comprise one, four, eight or sixteen sessions of durations equal to a day, a week, two weeks or four weeks, respectively.

The second phase preferably takes place a certain time after the last learning session (for example 24 hours, 48 hours or seven days). It can comprise several sessions of tests, of variable durations and under different experimental conditions.

The experimental conditions make it possible to generate a particular craving in the mice, and in particular with respect to one of the activities or one of the stimuli that they are able to find in the device. For example, the mice can be deprived of drink or food for some hours (for example of the order of 20 h).

The mice can also be subjected to particular treatment in order to cause particular deficiencies, preferably in relation to their memory and/or their ability to find their bearings. By way of non-limitative example, the quality of the mice's topographical memory can be tested by inducing a pathological state, in the non-transgenic models of Alzheimer's disease or at an age at which transgenic animals develop the first symptoms, for example animals overexpressing mutated forms of human APP (APP: Amyloid Precursor Protein) and triggering Alzheimer's disease spontaneously.

Certain mice can also undergo the second phase without having been subjected to any stress in order to highlight certain behavioural differences.

During the second phase, the mice can be put back into the device, individually or collectively.

A device according to the invention is suitable for studying mice of any type of lines, such as C57BL/6 or Swiss, for example.

More particularly, the plurality of means of stimulation comprises at least one means for:
  giving food to at least one mouse, and/or
  giving drink to at least one mouse, and/or
  causing at least one mouse to play, and/or
  causing at least one mouse to run, and/or
  putting at least one mouse in the presence of another mouse,
  each means of stimulation being utilized inside one house, and each house comprising only a single type of means of stimulation.

It is thus possible to stimulate at least one mouse by well defined, independent stimuli, thus making it possible to devise a plurality of stress situations and measure the influence of one or more deprivations on the general behaviour of the at least one mouse, and more particularly on its ability to find its bearings in the device.

It is thus possible, by means of the present device, to carry out tests for characterizing autism, and/or the feeding behaviour of the mice, and/or their social interaction and/or the movement sciences and/or the state of depression of a mouse population.

Preferably, the plurality of means of stimulation can comprise a food distributor and the plurality of sensors can comprise at least one sensor arranged for measuring the volume of food eaten by at least one mouse and/or the number of usages of said food distributor and/or the time spent using it.

Moreover, the travel time for going to the house comprising the means for giving food to the at least one mouse as well as the number of errors in getting there are two parameters that are measured and calculated.

In a particular embodiment, the food distributor can comprise:
- a main reservoir for food,
- a feeding reservoir connected to the main reservoir, and
- a flap (motorized or not) located between the main reservoir and the feeding reservoir, said flap being arranged to open and close automatically depending on the level of food present in the feeding reservoir.

Advantageously and applicable to the various embodiments of the invention, the plurality of means of stimulation comprises at least one drink distributor and the plurality of sensors comprises at least one sensor arranged for measuring the volume of liquid drunk by the at least one mouse and/or the number of times each drink distributor is used and/or the time spent using it.

Moreover, the travel time for going to the house comprising the means for giving drink to the at least one mouse as well as the number of errors in getting there are two parameters that are measured and calculated.

In a particular embodiment, the means for giving drink to the at least one mouse can comprise:
- at least one reservoir containing a liquid, and
- a teat located at the base of said reservoir.

Preferably, the means for giving drink comprises at least two reservoirs so as to be able to carry out a comparative study of the intake of plain water or of sugar water by the mice and thus measure their hedonic state.

Preferably and applicable to the various embodiments of the invention, the plurality of means of stimulation comprises a games platform comprising at least one tube arranged so that the at least one mouse can pass through it.

Advantageously, the at least one tube is made of a translucent material so that the mouse that is inside it can be seen, for example made of Plexiglas, glass or a plastic that is transparent to infrared light.

In this case the plurality of sensors can also comprise a camera for measuring the activity of the at least one mouse in the at least one tube.

Advantageously and applicable to the various embodiments of the invention, the plurality of means of stimulation comprises a running platform comprising at least one activity wheel.

In this case, the plurality of sensors can also comprise at least one sensor for measuring the number of revolutions of the wheel carried out and/or the average speed and/or the instantaneous speed and/or the usage time of each activity wheel.

Preferably and compatible with all the embodiments of the invention, the plurality of means of stimulation comprises an openwork cage of dimensions suitable for receiving another mouse and arranged to allow the at least one mouse located in the house to touch the other mouse located in said cage.

The cage is placed in one of the houses in such a way that a mouse entering the house can interact with the mouse enclosed in the cage, and preferably touch it with the end of its nose and/or with the end of at least one paw.

The cage is preferably made of a grating, the mesh of which allows establishment of this type of physical contact between mice.

In this case, the plurality of sensors can comprise a camera for measuring the interaction of the at least one mouse with the other mouse.

In particular, the following additional parameters finally make it possible to characterize, in a quantifiable manner, certain aspects of the behaviour of the mice and of their faculty for orientation in the device:
- the number of times and the volume of water taken,
- the number of times and the quantity of food taken,
- the number of revolutions of wheels, the duration of physical activity,
- the duration of social interaction,
- the time spent in the tunnels.

In particular and applicable to the various embodiments of the invention, the plurality of sensors comprises at least one sensor for detecting and measuring the movements of the at least one mouse inside the maze. For this purpose, said at least one sensor for detecting and measuring the movements of the at least one mouse inside the maze is arranged for detecting and tracking the shadow cast by the at least one mouse on the floor of the maze, by determining its centre of gravity for example, or its nose for more accurate tracking of its interactions with the device in a general way.

This sensor makes it possible to measure more particularly the movements of the at least one mouse in the maze and its demeanor in the maze (streets and/or houses). As explained above, these measurements, and/or those carried out for each house and for each activity, make it possible to calculate a certain number of parameters that make it possible, in particular by statistical processing of the data measured for each mouse of the plurality of mice introduced into the device, to characterize the quality of the geographical memory of such mice.

Moreover, the travel time for going to the houses comprising respectively the means for giving drink and food to the at least one mouse as well as the number of errors in getting there are two parameters that are measured and calculated.

In this case, at least a part of the floor of said device can be made of a material that is transparent to infrared radiation.

Preferably, the device can further comprise:
- at least one infrared source located on a first side of the device and arranged to illuminate the floor of said device uniformly, and
- at least one camera sensitive to infrared radiation located on a second side of the device and arranged for measuring the movements of the at least one mouse in the maze by detecting its shadow on the floor of said device.

It is thus possible to accurately measure the paths of each mouse inside the device, each mouse moreover being able to be identified by any marker.

Preferably, the diodes, which emit in the infrared, are arranged for providing backlighting of the floor of the device according to the invention; and the infrared camera is positioned at a sufficient height to track the at least one mouse in all of the elements of the device. The device is preferably constituted by plastic that is transparent to infrared radiation.

According to another aspect of the invention, applicable with any one of the embodiments of the first aspect, a method is proposed for evaluating the ability of the at least one mouse to orientate itself in the device according to the invention [any one of the preceding claims], said method comprising:

at least one learning step consisting of leaving said at least one mouse in the device for a predetermined time, called the learning time, a step of depriving said at least one mouse of water and/or of food for a period of time called the deprivation time, a testing step, during which the at least one mouse is put back into the device, the processing unit determines the number of errors made on the path to each house and/or the travel time for entering each house and/or the path taken.

BRIEF DESCRIPTION OF THE DRAWINGS

Other advantages and characteristics of the invention will also become apparent on the one hand from the following description and on the other hand from several embodiments given by way of indication and non-limitatively with reference to the attached schematic drawings, in which:

FIG. 1 shows a top view of the device according to the invention,

FIG. 2 shows a profile view of the device according to the invention,

DETAILED DESCRIPTION

Figure 3:
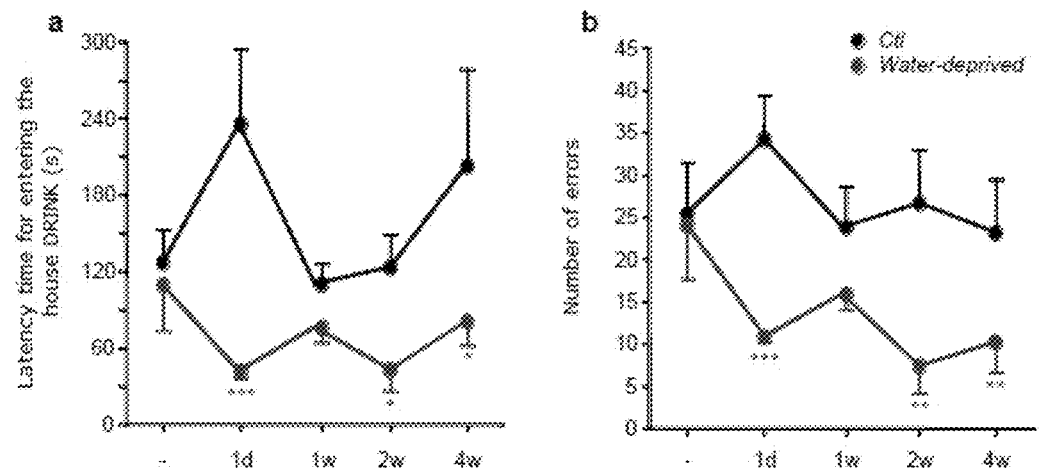
FIG. 3 shows the performance of the animals deprived of water and tested 24 hours after familiarization with the device.

The embodiments which will be described below are in no way limitative; it is possible in particular to imagine variants of the invention comprising only a selection of characteristics described below in isolation from the other characteristics described, if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

In particular, all the variants and all the embodiments described can be combined with each other if there is no objection to this combination from a technical point of view.

In the figures, the elements common to several figures retain the same reference.

With reference to FIGS. 1 and 2, the device 100 according to the invention comprises a plurality of houses 111-115—here five in number—distributed around a central space called the agora 150 and connected to each other by traffic means, called streets, 161-165, 171-175, 181-185 forming a maze.

The maze thus formed is preferably in the shape of a five-pointed star, in which the houses 111-115 each occupy an apex. The obstacles 141-145 are located in the middle of the arms of the star and make it possible to define in particular two traffic loops:

an outer traffic loop comprising the traffic means 161-165 and thus defining the shortest means for connecting two successive houses;

an inner traffic loop 171-175 that surrounds the agora 175 located at the centre of the star.

The outer traffic loop 161-165 is connected to the inner traffic loop 171-175 via passageways 181-185 which make it possible to avoid the obstacles 141-145.

Preferably, the outer side walls of the traffic means 161-165 forming the outer traffic loop are of a height such that the at least one mouse cannot get over it and get out of the device 100.

Advantageously, the outer side walls of the traffic means 161-165 forming the outer traffic loop are made of a translucent material so as to be able to observe the at least one mouse moving about inside and allow the animal to make use of its spatial memory on these outer traffic paths by utilizing external reference points linked to the configuration of the room and of the device and thus reinforce its cartographic and/or topographical memory of said device.

Thus, the houses 111-115 are all located at an equal distance from the agora 150 and have the same number of possible paths for reaching them from the agora 150, the direct paths all being of the same length. In other words, the houses 111-115 are arranged in such a way that the probability of reaching them from the agora 150 is the same for each of them.

The houses 111-115 are of sufficient sizes for at least one mouse to be able to enter and move about inside. In particular, they are of a sufficient height for the at least one mouse to be able to stand upright.

Advantageously, the dimensions of the sides of the houses are approximately 280 mm×160 mm, for a height of 300 mm.

Each house 111-115 has an opening 241-245 allowing the at least one mouse to enter and leave.

Each opening 241-245 of each house 111-115 opens onto a traffic space 161-165 allowing the at least one mouse to walk about in the device 100.

The device 100 according to the invention takes the form of a maze comprising the plurality of traffic spaces 161-165 and 171-175, the houses 111-115 and obstacles 141-145.

In the embodiment illustrated in FIGS. 1 and 2, the obstacles 141-145 are of such a height that the mice, even standing upright on their hind legs, cannot see the houses 111-115 on the other side. Typically, the height of the obstacles is at least equal to the height of the houses, for example 300 mm.

In the example illustrated in FIGS. 1 and 2, each house 111-115 comprises a means of stimulation for mice. This means makes it possible to stimulate at least one of the mouse's senses and/or allow it to carry out an activity.

Thus, the house 111 comprises at least one activity wheel 130, which the at least one mouse can enter and in which it can run, the wheel rotating about a fixed axis of rotation. The house 111 is called RUN in the following paragraphs.

Additionally, the house 111 can also comprise at least one sensor 131 for measuring the activity of the mouse with said activity wheel. Typically, but not limitatively, the at least one sensor 131 can be of the speed sensor type mounted on the activity wheel in order to measure the average and instantaneous rotary speed, the acceleration, a rev counter for measuring the number of revolutions made and a chronometer for measuring the duration of use of said activity wheel. A system based on the Spontaneous Activity Wheel from Bioseb can be envisaged (www.bioseb.com/bioseb/anglais/default/item_id=40.php).

The house 112 comprises a cage 122 occupying at least a part of the space of said house 112, and into which a mouse is introduced. Preferably, it is a mouse of the opposite sex to those moving about in the device 100. The cage 122 is arranged so that the mouse that is enclosed there can interact with the at least one mouse that enters the house 112. Typically, the cage 122 comprises a grating the mesh of which is sufficiently spaced for the mice to push the ends of their noses through and/or establish physical contact with each other, on either side of said cage 122. The house 112 is called INTERACT in the following paragraphs.

Additionally, the house 112 can also comprise at least one sensor 132 for measuring the activity of the mouse in said house 112, and more particularly its interaction with the mouse enclosed in the cage 122. Typically, but not limitatively, the at least one sensor 132 can be of the camera type so as to be able to study the behaviour of the mice in the house 112, and/or identify certain particular demeanours, revealing certain behavioural pathologies or deviances, for example the time and the number of direct contacts between a mouse and the animal placed in the compartment behind the grating.

The house 113 comprises at least one activity tube 123, which the at least one mouse can enter and walk in, and that it can pass through freely. Preferably, the at least one tube is located on the horizontal and/or slightly raised relative to the floor. The house 113 is called PLAY in the following paragraphs.

Additionally, the house 113 can also comprise at least one sensor 133 for measuring the activity of the mouse with the at least one activity tube 123, for example made of transparent Plexiglas. Typically, but not limitatively, the at least one sensor 133 can be of the camera type in order to study the behaviour of the at least one mouse in the tube and/or a certain particular demeanour and reveal certain behavioural pathologies or deviances, for example the time spent in the at least one tube and/or the number of times that the at least one mouse enters said tube.

The house 114 comprises a food dispenser 124 arranged so that a mouse can eat there with total autonomy. Preferably, the food dispenser 124 is of the automatic granule distributor type, comprising a main reservoir 126 for food granules, a secondary reservoir connected to the main reservoir via an automatic door that allows the secondary reservoir to be filled when it is empty or below a certain threshold. The at least one mouse can thus eat freely from the secondary reservoir. The house 114 is called EAT in the following paragraphs. The main reservoir 126 includes a feeding reservoir 127 connected to the main reservoir, and a flap 128 (motorized or not) located between the main reservoir and the feeding reservoir, the flap being arranged to open and close automatically depending on the level of food present in the feeding reservoir.

Additionally, the house 114 can also comprise at least one sensor 134 for measuring the activity of the mouse with the dispenser 124. Typically, but not limitatively, the at least one sensor 134 can be arranged for measuring the volume of food ingested by the at least one mouse at each intake, the number of times that it uses said dispenser 124 and/or its time of use. Moreover, the at least one sensor 134 also makes it possible to measure each feed intake (each mouthful), its date and time, its duration, and the quantity ingested. An automated system of the BioDAQ type from Research Diets Inc. can be used (www.researchdiets.com/biodaq/applications/food-water-intake).

Finally, the house 115 comprises at least one liquid dispenser 125 and a teat 129 located at the base of said dispenser that dispenses the liquid from the dispenser. Preferably, the house 115 comprises two dispensers 125 so as to be able to carry out measurements of hedonism, the first dispenser comprising for example a solution of sugar water and the second dispenser comprising a solution of plain water. Preferably, the dispenser 125 contains a liquid that is edible by the at least one mouse. The dispenser 125 can comprise a reservoir arranged to contain a given volume of liquid and a pipette to allow the at least one mouse to drink autonomously. The house 115 is called DRINK in the following paragraphs.

Additionally, the house 115 can also comprise at least one sensor 135 for measuring the activity of the mouse with the liquid dispenser 125. Typically, but not limitatively, the at least one sensor 135 can be arranged for measuring the volume of each portion of water taken by the at least one mouse, the number of times that it uses said dispenser 125 and/or its time of use. An automated system of the BioDAQ type from Research Diets Inc. can be used (www.researchdiets.com/biodaq/applications/food-water-intake).

As illustrated in FIG. 2, the device 100 according to the invention can also comprise at least one sensor called an environment sensor 210 arranged for measuring the general activity of the at least one mouse in the device 100, and in particular its movements in the maze.

Advantageously, the at least one sensor 210 can be of the camera type, with a field of view at least partly covering the device 100.

In a clever way, the movement of the at least one mouse can be measured by a technique based on tracking the shadow cast by the at least one mouse on the floor 230. For this purpose, at least one lighting source 221-224 is arranged on one side of the device 100 so as to illuminate the floor of the latter uniformly.

Preferably, the at least one lighting source 221-224 is located under the floor of said device.

Advantageously, the at least one lighting source 221-224 is of the infrared source type so that the mice are not perturbed and/or influenced by the illumination of the floor 230.

In this particular embodiment, the floor 230 is transparent to the radiation emitted by the at least one lighting source 221-224, and the at least one environment sensor 210 is sensitive to infrared radiation. Thus, when the at least one mouse moves on the floor, the sensor 210 detects less light at the location of said mouse. It is therefore possible for the movement of the at least one mouse throughout the maze to be measured efficiently and at less cost.

The device also comprises a processing unit 211 that makes it possible to utilize all of the data measured by the various sensors 121-125 located in each house 111-115, as well as by the at least one environment sensor 210. The data measured are collected according to a protocol defined by the user (drawings of the areas of interest, monitoring thresholds of the animals, duration of acquisition, time intervals for collection of information, etc.). The final data are preferably presented in the form of a spreadsheet in a very versatile format to allow the user to apply their own calculation macros.

By way of non-limitative examples, the following parameters can be calculated from the data from the set of sensors 121-125, 210:

The number of times that each of the houses 111-115 and the agora 150 are entered.

The time spent entering the houses 111-115, and more particularly those where the at least one mouse can drink 115 and eat 114.

The number of errors in reaching the houses 111-115, and more particularly those where the at least one mouse can drink 115 and eat 114.

All of the paths taken by each mouse present in the device 100.

Numbers of times each of the traffic spaces 161-165, 171-175 and 181-185 are entered.

The speed of progression of each mouse in the device 100.

The interaction between each mouse present in the device 100.

The number and the place of the rearing activities of each mouse.

The number and the place of the grooming activities of each mouse.

The number and position of the changes of paths of each mouse in the device 100 (U-turns).

The number and volume of water intakes, and the time spent in the corresponding house.

The number and quantity of food intakes, and the time spent in the corresponding house.

The number of revolutions of wheels, the time of physical activity, and the time spent in the corresponding house.

The time of social interaction and the time spent in the corresponding house.

The time spent in the tunnels and the time spent in the corresponding house.

The present invention thus relates to a device for studying the ability of the at least one mouse to find its bearings in a maze, said device comprising a plurality of houses distributed around a central agora, in which means of stimulation allow the at least one mouse to carry out certain activities and/or satisfy certain primary needs. Each house further comprises at least one sensor for measuring the activity of the mouse in said house, and more particularly its use of the means of stimulation. Finally, a sensor makes it possible to detect and measure the movements of each mouse in the device. Quantitative parameters originating from these measurements thus make it possible to highlight the quality of the geographical memory of the at least one mouse.

Several examples of tests and of usage of the device according to the invention will now be described:

behaviour of the mice after 4 days of familiarization: in the course of a first series of experiments, the mice were trained for 4 days (4 h per day), allowing them to move about freely in the device. 24 h after the last training session, the animals were placed individually in the device and their exploration was measured and analysed for 10 min. The latency for entering each house, the number of entries and the total time spent in each house are presented in Table 1.

| Parameter | Houses | | | | | Agora |
|---|---|---|---|---|---|---|
| | Drink | Eat | Run | Interact | Play | |
| Latency (s) | 93 ± 17 | 86 ± 26 | 49 ± 13 | 74 ± 25 | 120 ± 35 | |
| Duration (s) | 20 ± 4 | 67 ± 10 | 200 ± 38 | 88 ± 19 | 65 ± 16 | 11 ± 2 |
| Number of entries | 2.8 ± 0.3 | 4.9 ± 0.9 | 7.3 ± 0.9 | 5.6 ± 0.8 | 4.3 ± 0.8 | 7.5 ± 1.1 |

The mice tend to explore the various houses differently, with the highest number of entries in the house Run and the lowest scores in the house Drink. However, all the houses are properly recognized by the animals, suggesting that they explore the entire complexity of the apparatus effectively.

Memorization of the mice in the device after 4 days of familiarization: the topographical learning of the mice is then tested; they are deprived of water or of food for 20 h before being put back into the device. The periods of familiarization varied from zero to 1 day, 1, 2 or 4 weeks. In this experiment, the performance of the animals was measured and analysed, and more particularly the latency time for entering the house DRINK or EAT as well as the number of errors made between the agora and each of the houses.

Figure 4:
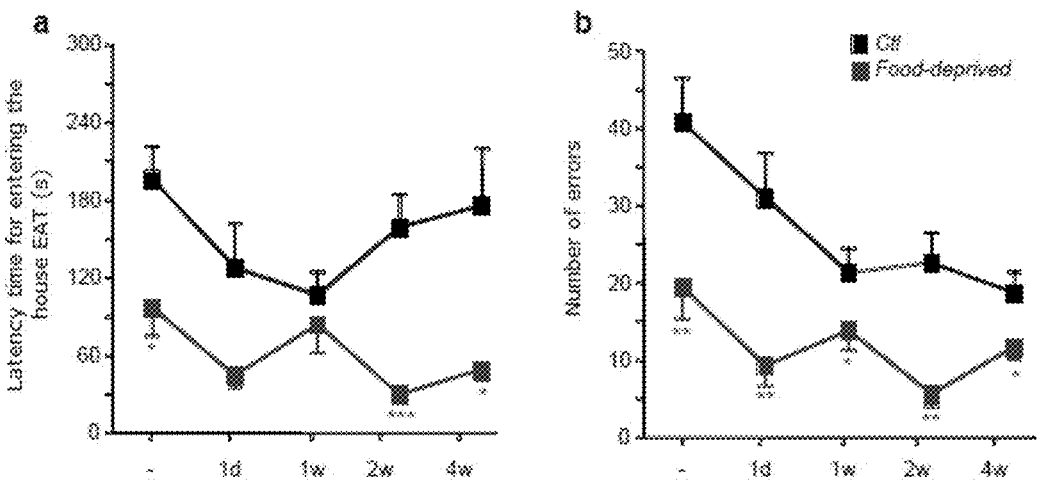
FIG. 4 shows the performance of the animals deprived of food and tested 24 hours after familiarization with the device.

The results for the animals deprived of drink are presented in FIG. 3, and the results obtained for the animals deprived of food are presented in FIG. 4, in each case compared to control animals (Ctl).

As can be seen in FIG. 3, it appears that the animals that are not deprived show moderate performance, whatever the period of familiarization, with an average latency of 156 s for entering the house DRINK and an average number of errors of 27 ($R2=0.012$ for the latency and $R2=0.183$ for the number of errors). On the other hand, the animals deprived of water show latencies and numbers of errors that decrease significantly with the period of familiarization, and significantly after 1 day, 2 or 4 weeks of familiarization. The profile of the errors decreases significantly with the sessions ($R2=0.563$).

FIG. 4 shows the performance for the animals deprived of food. The animals that were not deprived show moderate performance whatever the period of familiarization, in terms of latency for entering the house EAT (average of 148 s, $R2=002$). However, surprisingly, the number of errors decreases with the sessions ($R2=0.847$). On the other hand, the animals deprived of food show latencies and numbers of errors that are significantly reduced, particularly after 2 or 4 weeks of familiarization. Moreover, the latencies and numbers of errors are lower than for the control animals without familiarization. The profiles of the measurements relating to the animals that were deprived decrease significantly with the numbers of sessions ($R2=0.381$ for the latencies and $R2=0.343$ for the numbers of errors).

Topographical disorientation following amyloid toxicity: the objective here is to determine whether a pathological state of the Alzheimer type can induce forgetting of the topographical memory in the mice. For this purpose, a batch of animals was familiarized with the device over 2 weeks. Then their learning was tested for a first time after water deprivation. Finally, they were injected with a preparation of oligomers of Aβ25-35 peptide by the intracerebroventricular route. This preparation represents an acute model of Alzheimer's disease that is often used in the laboratory.

Figure 5:
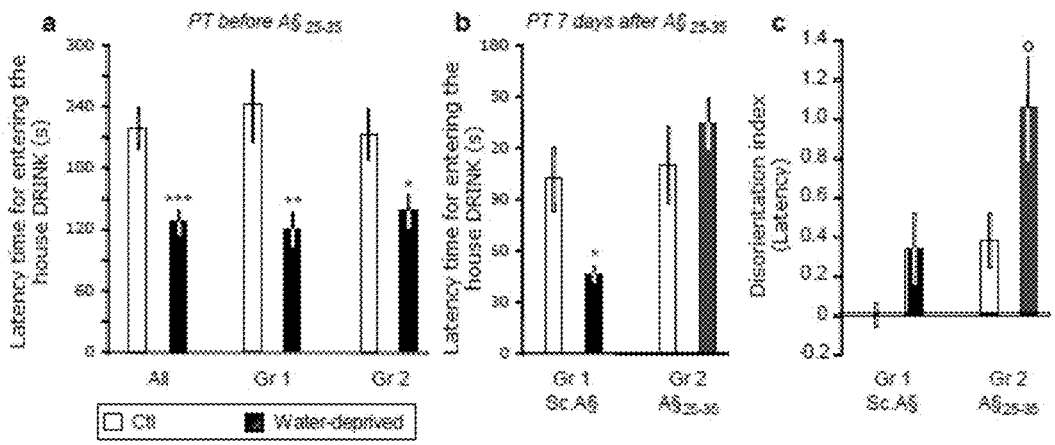
FIG. 5 shows the performance of healthy animals deprived of water and tested 24 hours after familiarization with the device, and then contaminated with an acute model of Alzheimer's disease and tested again after 7 days; as well as an index of discrimination.

The results are presented in FIG. 5. For the animals that had assimilated the location of the house DRINK and on the day of the test showed significantly lower latency than the control group without deprivation, injection of amyloid peptide induces amnesia, which is not observed for the group treated with the control peptide. The latter are always as efficient, or even more efficient, at remembering the location of the house DRINK even 8 days after the end of familiarization.

A simple calculation makes it possible to define a disorientation index (DI):

$$DI=(PT7/PT0)-(PT7/PT0)_{control\ group}$$

with PT7=value of the memory test 7 days after injection of $A\beta_{25-35}$ peptide, PT0=value of the memory test immediately before injection of $A\beta_{25-35}$.

Thus, this index is zero for the control animals (mice not deprived of water and injected with a non-toxic Sc.Aβ peptide) and significantly higher in the animals treated with the amyloid peptide $A\beta_{25-35}$, making it possible to propose pharmacological studies for testing whether candidate drug molecules attenuate or block the increase of this index, and therefore topographical disorientation.

Familiarization in the device according to the invention therefore constitutes a rich and complex environment, which affects brain plasticity and neurogenesis of the hippocampus.

The present invention thus allows quantitative measurement of animal behaviour, in particular in the context of neuropharmacology and preclinical animal research, in particular aimed at measurement of learning processes based on the spontaneous latent exploration of a complex environment and processes of familiarization of the mice with this environment.

The present device makes it possible to measure significant differences between the behaviour of the animals with familiarization and of the animals without familiarization in an amnesia test (for water or food). The period of familiarization can vary from one day to 4 weeks or over a longer period.

The present device is able to measure the impact of cognitive deficits in particular associated with age, with pharmacological models of amnesia (treatment with scopolamine, for example), with pharmacological and genetic models of dementia (as illustrated here with the injection of amyloid peptide, but also transgenic lines of Alzheimer's disease) and other debilitating conditions (stressed or depressive animals, for example).

The present invention thus in particular makes it possible to analyse one of the important early warning signs for Alzheimer's disease: the symptom of spatial disorientation.

According to one of the embodiments, the device makes it possible to characterize autism.

According to one of the other embodiments, the device makes it possible to characterize feeding behaviour.

According to one more the other embodiments, the device makes it possible to characterize social interaction.

According to one more the other embodiments, the device makes it possible to characterize the movement sciences.

According to one more the other embodiments, the device makes it possible to characterize the state of depression of a mouse population.

Of course, the invention is not limited to the examples which have just been described and numerous adjustments can be made to these examples without exceeding the scope of the invention. In particular, the different characteristics, forms, variants and embodiments of the invention can be combined with one another according to various combinations inasmuch as they are not incompatible or mutually exclusive. In particular all the variants and embodiments described previously can be combined with each other.

The invention claimed is:

1. A device for studying the topographical memory of at least one mouse, the device comprising:
   a central space, called the agora, open on at least one side;
   a plurality of closed spaces, called houses, located at the periphery of the agora, said houses being open on one side and connected to at least one traffic space, called a street, allowing the at least one mouse to reach the agora;
   a plurality of means of stimulation of the at least one mouse located in the plurality of houses; and
   said at least one traffic space forms a maze that is arranged in such a way that the distances between the agora and each house are identical, each house being accessible from the agora via at least two direct paths of the same length, all of the direct paths connecting each house to the agora being of equal length.

2. The device according to claim 1, further comprising:
   a plurality of sensors arranged for measuring the activity of the at least one mouse with the plurality of means of stimulation; and
   a processing unit arranged for determining behavioral parameters of the at least one mouse in said device from measurements made by the plurality of sensors.

3. The device according to claim 2, wherein the plurality of means of stimulation comprises a food distributor, and in that the plurality of sensors comprises at least one sensor arranged for measuring the volume of food eaten by the at least one mouse and/or the number of usages of said food distributor and/or the time spent using it.

4. The device according to claim 3, wherein the food distributor comprises:
   a main reservoir for food and a feeding reservoir connected to the main reservoir; and
   a flap located between the main reservoir and the feeding reservoir, said flap being arranged to open and close automatically depending on the level of food present in the feeding reservoir.

5. The device according to claim 2, wherein the plurality of means of stimulation comprises at least one drink distributor and in that the plurality of sensors comprises at least one sensor arranged for measuring the volume of liquid drunk by the at least one mouse, the number of times each drink distributor is used or the time spent using it.

6. The device according to claim 5, wherein the drink distributor comprises:
   at least one liquid dispenser containing a liquid; and
   a teat located at the base of said liquid dispenser.

7. The device according to claim 2, wherein the plurality of means of stimulation comprises a games platform comprising at least one tube arranged so that the at least one mouse can pass through it, and in that the plurality of sensors comprises a camera for measuring the activity of the at least one mouse in the at least one tube.

8. The device according to claim 2, wherein the plurality of means of stimulation comprises a running platform comprising at least one activity wheel, and in that the plurality of sensors comprises at least one sensor for measuring the number of revolutions of the wheel carried out, the average speed, the instantaneous speed or the usage time of each activity wheel.

9. The device according to claim 2, wherein the plurality of means of stimulation comprises an openwork cage of dimensions suitable for receiving another mouse and arranged to allow the at least one mouse located in the house to touch the other mouse located in said cage, and in that the plurality of sensors comprises a camera for measuring their interaction.

10. The device according to claim 2, wherein the plurality of sensors comprises at least one sensor for detecting and measuring the movements of the at least one mouse inside the maze.

11. The device according to claim 10, wherein at least a part of the floor of said device is made of a material that is transparent to infrared radiation.

12. The device according to claim 11, further comprising:
at least one infrared source located on a first side of the device and arranged for uniformly illuminating the floor of said device; and
at least one camera sensitive to infrared radiation located on a second side of the device and arranged for measuring the movements of the at least one mouse in the maze by detecting its shadow on the floor of said device.

13. A method for evaluating the ability of at least one mouse to orientate itself in a device for studying the topographical memory of the at least one mouse wherein the device includes a central space, called the agora, open on at least one side, a plurality of closed spaces, called houses, located at the periphery of the agora, said houses being open on one side and connected to at least one traffic space, called a street, allowing the at least one mouse to reach the agora, a plurality of means of stimulation of the at least one mouse located in the plurality of houses where said at least one traffic space forms a maze that is arranged in such a way that the distances between the agora and each house are identical, each house being accessible from the agora via at least two direct paths of the same length, all of the direct paths connecting each house to the agora being of equal length, the method comprising:
at least one learning step consisting of leaving said at least one mouse in the device for a predetermined time, called the learning time;
a step of depriving said at least one mouse of at least one of water and food for a period of time, called the deprivation time;
a testing step, during which the at least one mouse is put back into the device; and
an error determination step in which the processing unit determines the number of errors made on the path to each house, the travel time for entering each house, or the path taken by the at least one mouse.

14. The method according to claim 13, further comprising a step of constructing the device to further include:
a plurality of sensors arranged for measuring the activity of the at least one mouse with the plurality of means of stimulation, wherein at least one sensor of said plurality of sensors is configured to detect and measure movements of the at least one mouse inside the maze; and
a processing unit arranged for determining behavioral parameters of the at least one mouse in said device from measurements made by the plurality of sensors.

* * * * *